(12) United States Patent
Mansson et al.

(10) Patent No.: US 8,658,381 B2
(45) Date of Patent: Feb. 25, 2014

(54) DETECTION CONJUGATE

(76) Inventors: Alf Mansson, Kalmar (SE); Sven Tagerud, Nybro (SE)

(*) Notice: Subject to any disclaimer, the term of this patent is extended or adjusted under 35 U.S.C. 154(b) by 711 days.

(21) Appl. No.: 12/517,148

(22) PCT Filed: Nov. 30, 2007

(86) PCT No.: PCT/SE2007/001071
§ 371 (c)(1),
(2), (4) Date: Jun. 1, 2009

(87) PCT Pub. No.: WO2008/066463
PCT Pub. Date: Jun. 5, 2008

(65) Prior Publication Data
US 2010/0248212 A1 Sep. 30, 2010

(30) Foreign Application Priority Data
Dec. 1, 2006 (SE) .................................. 0602571-2

(51) Int. Cl.
*G01N 31/00* (2006.01)
*G01N 33/53* (2006.01)

(52) U.S. Cl.
USPC ............ 435/7.21; 435/7.1; 436/501; 436/518; 424/9.1; 424/520; 422/430; 530/300; 530/350

(58) Field of Classification Search
None
See application file for complete search history.

(56) References Cited

PUBLICATIONS

Kim et al. (Analytica Chimica Acta, 2006, vol. 577, p. 163-170).*
Bachand et al. "Active Capture and Transport of Virus Particles Using a Biomolecular Motor-Driven, Nanoscale Antibody Sandwich Assay." *SMALL*. vol. 2. No. 3. 2006. pp. 381-385.
Balaz et al. "Detection of small differences in actomyosin function using actin labeled with different phalloidin conjugates." *Anal. Biochem.* vol. 338. 2005. pp. 224-236.
Besteman et al. "Enzyme-Coated Carbon Nanotubes as Single Molecule Biosensors." *Nano Letterws.* vol. 3. No. 6. 2003. pp. 727-730.
Briand et al. "Immoboilization of Protein A on SAMS for the elaboration of immunosensors." *Colloids and Surfaces B. Biointerfaces* vol. 53. 2006. pp. 215-224.
Cathala et al. "Laboratory Methods: A Method for Isolation of Intact Translationally Active Ribonucleic Acid." *DNA.* vol. 2. No. 4. 1983. pp. 329-335.
D'Orazio. "Biosensors in clinical chemistry." *Clinica Chimica Acta.* vol. 334. 2003. pp. 41-69.
El-Kouedi et al. "Biofunctionalized Nanoparticles for Surface-Enhanced Raman Scattering and Surface Plasmon Resonance." *Nanobiotechnology. Wiley-Vch.* 2004. pp. 429-443.
Gittes et al. "Flexural Rigidity of Microtubules and Actin Filaments Measured from Thermal Fluctuations in Shape." *J. of Cell Biol.* vol. 120. No. 4. 1993. pp. 923-934.
Goddard et al. "Biomolecules as nanomaterisl: interface characterization for sensor development." *Proc. of SPIE* vol. 6172. pp. 617206-1-617206-12.
Hirabayashi et al. "Malachite Green-Conjugated Microtuules as Mobile Bioprobes Selective for Malacite Green Aptamers with capturing/releasing Ability." *Biotech. and Bioengin.* vol. 94. No. 3. 2006. pp. 473-480.
Homsher et al. "Factors affecting movement of F-actin filaments propelled by skeletal muscle heavy meromyosin." *Am. J. Physiol.* vol. 262. 1992. pp. C714-C723.
Kim et al. "Real-time observation of temperature-dependent protein-protein interactions using real-time dual-color detection system." *Anal. Chimica Acta.* vol. 577. 2006. pp. 163-170.
Kinosian et al. "$Ca^{2+}$ Regulation of Gelsolin Activity: Binding and Severing F-actin." *Biophysical J.* vol. 75. 1998. pp. 3101-3109.
Korneeva et al. "Light microscopic analysis of ligand-induced actin filament suprastructures." *Euro. J. of Cell Biol.* vol. 71. 1996. pp. 351-355.
Kron et al. "Assasy for Actin Sliding Movement over Myosin-Coated Surfaces." *Methods in Enzymology.* vol. 196. 1996. pp. 399-415.
Mansson et al. "In vitro sliding of actin filaments labeled with single quantum dots." *Biochem. and Biophys. Research Comm.* vol. 314. 2004. pp. 529-534.
Nam et al. "Nanoparticle-Based Bio-Bar Codes for the ultrasensitive Detection of Proteins." *Science.* vol. 301. 2003. pp. 1884-1886.
Ghatnekar-Nilsson et al. "Resonators with integrated CMOS circuitry for mass sensing applications fabricated by electron beam lithography." *Nanotechnology.* vol. 16. 2005. pp. 98-102.
Pardee et al. "Purification of Muscle Actin." *Methods in Cell Biol.* vol. 24. 1982. 10 pages.
Pejcic et al. "The role of biosensors in the detection of emerging infectious diseases." *Analyst.* vol. 131. 2006. pp. 1079-1090.
Ramachandran et al. "Selective Loading of Kinesin-Powered Molecular Shuttles with Protein Cargo and its Applications to Biosensing." *SMALL* vol. 2. No. 3. 2006. pp. 330-334.
Sase et al. "Real Time Imaging of Single Fluorophores on Moving Actin with an Epifluorescence Microscope." *Biophysical Journal.* vol. 69. 1995. pp. 323-328.
Smith et al. "Molecular pathogenesis of chronic myeloid leukaemia." *Expert Review.* vol. 5. 2003. pp. 1-27.
Sundberg et al. "Silanized surfaces for in vitro studies of actomyosin function and nanotechnology applications." *Anal. Biochem.* vol. 323. 2003. pp. 127-138.
Walker et al. "Dynamic Instability of Individual Microtubules Analyzed by Video Light Microscopy: Rate Constants and Transition Frequencies." *J. of Cell Biol.* vol. 107. 1988. pp. 1437-1448.
Zheng et al. "Multiplexed electrical detection of cancer markers with nanowire sensor arrays." *Nature Biotech.* vol. 23. No. 10. 2005. pp. 1294-1301.
International Search Report for PCT/SE2007/001071 mailed Mar. 26, 2008.
European Search Report for EP 07 852 077 mailed Feb. 9, 2010.

\* cited by examiner

*Primary Examiner* — Lisa Cook
(74) *Attorney, Agent, or Firm* — Merchant & Gould P.C.

(57) ABSTRACT

The invention relates to a detection conjugate composed of a filament fragment, e.g. a cytoskeletal filament such as actin filaments or microtubules, and recognition elements bound to this fragment as well as kits comprising said detection conjugate and methods how to use said detection conjugate as well as the use for the detection of one or more compounds present within a sample, such as a biological sample.

14 Claims, 3 Drawing Sheets

DETECTION CONJUGATE

This application is a National Stage Application of PCT/SE2007/001071, filed 30 Nov. 2007, which claims benefit of Ser. No. 0602571-2, filed 1 Dec. 2006 in Sweden and which application(s) are incorporated herein by reference. To the extent appropriate, a claim of priority is made to each of the above disclosed applications.

FIELD OF INVENTION

The invention relates to a detection conjugate comprising a filament fragment and reporter molecules and recognition elements bound to this fragment as well as kits comprising said detection conjugate and methods how to use said detection conjugate as well as the use for the detection of one or more compounds present within a sample, such as a biological sample.

BACKGROUND OF INVENTION

With an increasing globalisation as well as a growing population we are faced with different threats like terrorism, such as bioterrorism, influenza outbreaks and a number of environmentally hazardous chemicals. To be able to react in a fast and effective way whatever happens it is very important to develop cost effective detection methods which in a fast and reliable way can detect the presence of, for example, a pathogen (such as a bacterium or a virus) or a toxic compound (e.g. an environmental hazard). With a growing elderly population there is also a need of developing early detection methods which at an early stage can detect a disease or disorder, such as cancer or Alzheimer's disease for prevention or individualized and effective treatment.

Today, the above mentioned disease markers, pathogens and compounds are detected by the use of rather large sample volumes, such as in the μl range, e.g. in an Enzyme-linked immunosorbent Assay (ELISA). Additionally, the specificity and sensitivity of current detection methods is sometimes low. Commonly used methods are polymerase chain reaction (PCR), ELISA and enzyme-linked immunoassay (EIA). For the detection of microorganisms the said detection methods are often preceded by cultivation of the microorganism, e.g. virus or bacteria. Whereas this procedure increases the sensitivity of the method it also significantly decreases the speed of detection.

Presently several attempts are ongoing in which the detection methods are being miniaturised by the combination of antibodies, oligonucleotides or other recognition elements with state-of-the art nanotechnology[1,2]. Hereby, extremely complex techniques are developed which combine microfluidics systems with the binding of the different components to micro or nanostructured surfaces[3], wherein specific biological recognition elements are used. Detection of the binding between the compound and the antibodies or oligonucleotides can be determined by advanced methods such as altered conductance of nanowires[4] or carbon nanotubes[5] or altered resonance in a nano-cantilever[6]. In other cases increases in sensitivity have been obtained by the use of antibodies which have been bound to magnetic nanoparticles and the very specific identification obtained through oligonucleotide sequences[7]. In the different nanotechnology-related methods there is always a need to use different types of nanoparticles, nanowires etc. This is not completely unproblematic since the use of larger amounts of nanoparticles as well as nanotubes has an impact on the environment since they are potentially toxic. Additionally, methods based on state-of-the-art nanotechnology are presently complex and expensive. All the mentioned drawbacks may be reasons why these methods are not used on a large scale today. Thereby it is evident that there is a need for new techniques which are reliable, cost efficient and environmentally friendly at the same time as they are highly sensitive and with the potential to be used in a miniaturised system.

SUMMARY OF THE INVENTION

The invention relates to a novel approach with a new type of detection conjugates suspended in a solution or in a gel or flexibly attached to a surface. This method enables for the first time the possibility to use very small sample volumes as well as increasing the sensitivity to the compound/analyte to be detected as well as a possibility to detect different analytes in one and the same sample. Moreover, this method, unlike most previous biosensing methods does not rely on the binding of recognition elements to artificial surfaces. Accordingly the invention is a low cost method, wherein the recognition elements, such as antibodies are immobilized to filamentous binding fragment(s) which might be cytoskeletal filaments such as actin filaments or microtubules. In general the invention relates to the finding that binding fragments such as actin filaments and microtubules can bind recognition elements, such as antibodies and nucleic acid oligomers and at the same time bind reporter molecules (e.g. fluorophores) forming one or more detection conjugate(s). In a first aspect the invention relates to a detection conjugate comprising a binding fragment selected from the group consisting of cytoskeletal filaments and fragments and chemically modified versions thereof and at least one recognition element linked to said binding fragment as defined by the specific application.

In a second aspect the invention relates to a detection conjugate with increased sensitivity accomplished by attaching (a) reporter molecule(s) to the detection conjugate.

In a third aspect the invention relates to One or more detection conjugate(s) according to any of the preceding claims, wherein said conjugates become linked to each other via their bound recognition element(s) in the presence of analyte and thereby cross-link and aggregate.

In a fourth aspect the invention relates to a kit comprising several of said detection conjugates.

In a fifth aspect the invention relates to a method in which said detection conjugates are used for the detection of one or more compounds/analytes.

In a sixth aspect the invention relates to the use of said detection conjugates, kit or method for the detection of one or more analytes in a sample.

The detection conjugate(s) may identify a specific compound (analyte) in a sample and upon binding of the analyte to said binding fragment aggregation of the detection conjugates will occur wherein said aggregates can be detected by the use of different detection methods such as for example microscopy. Due to aggregation of detection conjugates an amplification of the sensitivity occurs and small amounts down to individual molecules can be detected. Moreover, several different components/compounds may be detected in one and the same sample if the proportions between different recognition elements on the binding fragments co-vary with the proportions of different reporter molecules.

DETAILED DESCRIPTION OF THE INVENTION

Definitions

Figure 1:
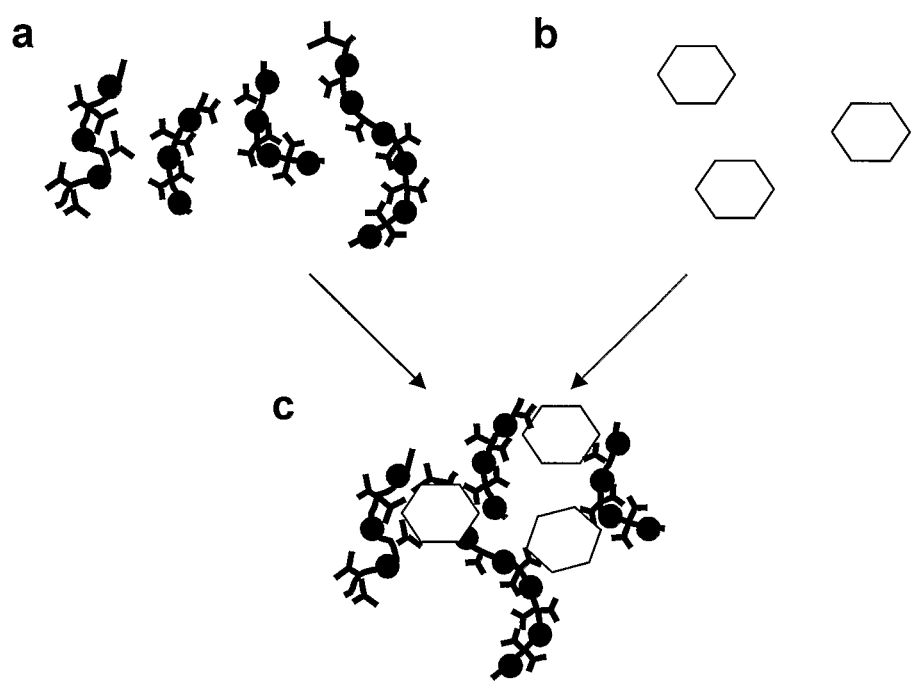
FIG. 1 is a schematic presentation showing the cytoskeletal filaments (curved lines) being coated by recognition elements exemplified by antibodies (Y) without any compound (analyte) to be detected (a). The cytoskeletal filaments are furthermore labelled with one or more reporter molecule(s). When the analyte (hexagone) is added (b) the cytoskeletal filaments aggregate (c). The formation of aggregates may be observed using a microscope or other methods.

In the context of the present application and invention the following definitions apply:

The term "binding fragment" is intended to mean an elongated fragment such as a filament having the ability to bind at least one recognition element and at least one reporter molecule. Examples are found below.

The term "recognition element or recognition molecule" is intended to mean anything having the ability to be bound to said binding fragment and also, with high specificity, to a compound (an analyte) to be detected in a sample. Examples are found below.

The term "reporter molecule" is intended to mean a molecule which binds to the binding fragment and forms the basis for the ability of the system to detect binding of an analyte to a recognition element. The term "reporter molecule" is also intended to mean a particle such as a quantum dot or other type of nano particle. Examples are found below.

A "detection conjugate" is one binding fragment, with or without bound reporter molecule(s), that has at least one recognition element bound. Examples are found below.

The term "analyte" is intended to mean a compound or a component which a person skilled in the art would like to detect in a sample. Examples are found below.

The Detection Method

In one embodiment the invention relates to a detection conjugate comprising a binding fragment being a cytoskeletal filament, fragments and parts thereof, variants thereof, synthetic versions thereof and chemically modified versions thereof and at least one recognition element coupled to said fragment covalently or via non-covalent specific affinity coupling. Examples of binding fragments are actin filaments and microtubules and prokaryotic analogues. Said recognition element may be selected from the group consisting of polyclonal and monoclonal antibodies, which may be genetically engineered monoclonal antibodies, such as chimeric or humanised monoclonal antibodies, other chimeric proteins, Fab-fragments of the mentioned types of antibodies, lectins, receptor proteins, nucleic acids, olignucleotides, aptamers, peptides, chemical compounds or fragments thereof. These may be coupled to the binding fragments covalently or via non-covalent specific affinity coupling (e.g. streptavidin-biotin). The filaments generally have a eukaryotic origin mainly from muscle (e.g. bovine heart) but may also be from other tissues such as skeletal muscle or brain (microtubules) or from cultured cells or tissues. However, filaments or filament analogues expressed in prokaryotes are other examples of binding fragments. The filaments may also be of mixed origin and they may also have a mixture of different lengths and be branched. The specific characteristic of different binding fragments is dependent, on among different things, the analyte to be detected and needs to be evaluated for each case, being obvious for a person skilled in the art. Several studies[8-10] have shown that it is possible to bind a number of particles along microtubules and actin filaments without any depolymerisation of the filaments and without preventing their interaction with the normal cellular binding partners such as specific types of molecular motors.

Monoclonal antibodies as recognition elements may be used in the detection of bacteria and virus particles since these have multiple copies of given epitopes (e.g. viral capsids) to which the same monoclonal antibodies can bind. The use of monoclonal antibodies is possible also for the detection of proteins having at least two epitopes to which the monoclonal antibodies can bind resulting in aggregation of at least two actin filaments.

For the detection of proteins of small or average size (<10 nm diameter; <200 kDa) it is probably better to use polyclonal antibodies but it might, however, also be possible with monoclonal antibodies. One example could be the use of monoclonal antibodies directed against different epitopes on one and the same protein thereby enabling aggregation of the binding fragments and also increasing the sensitivity and specificity, such as having one monoclonal antibody on one binding fragment and another one on the other binding fragment. If the molecule of interest to detect is very small it is possible to use aptamers in combination with antibodies to increase the sensitivity.

Figure 2:
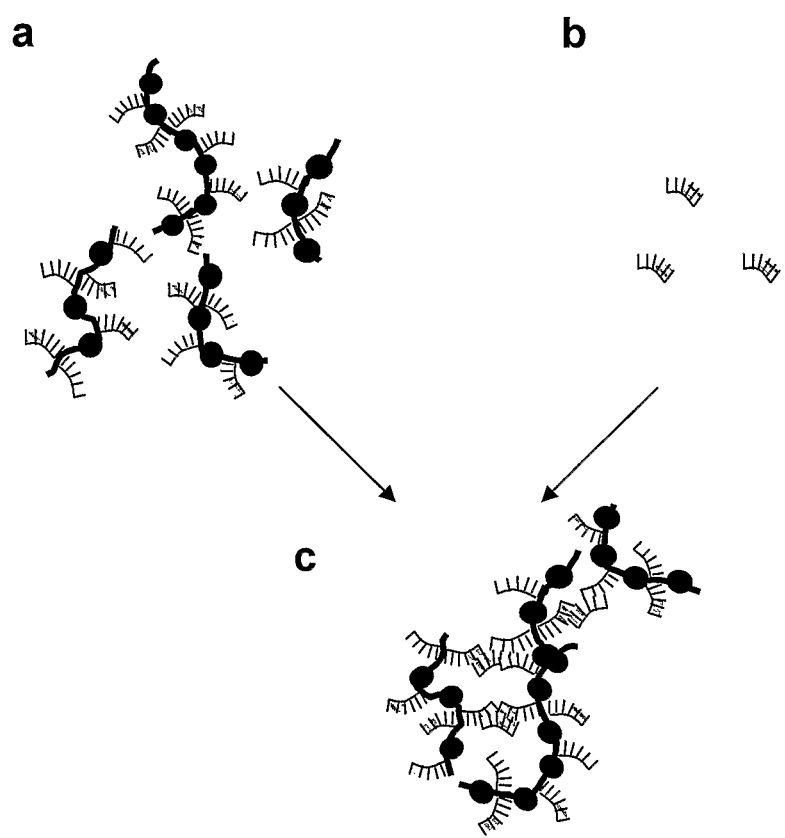
FIG. 2 is s schematic presentation showing cytoskeletal filaments (curved lines) being coated with recognition elements being exemplified by nucleic acid fragments/oligonucleotides (comblike structures) without any analyte present (a). The cytoskeletal filaments are also labelled with a reporter molecule (filled circle). When the component to be detected is added (b) the cytoskeletal filaments aggregate forming complexes which then can be detected in a variety of ways.
Figure 3:
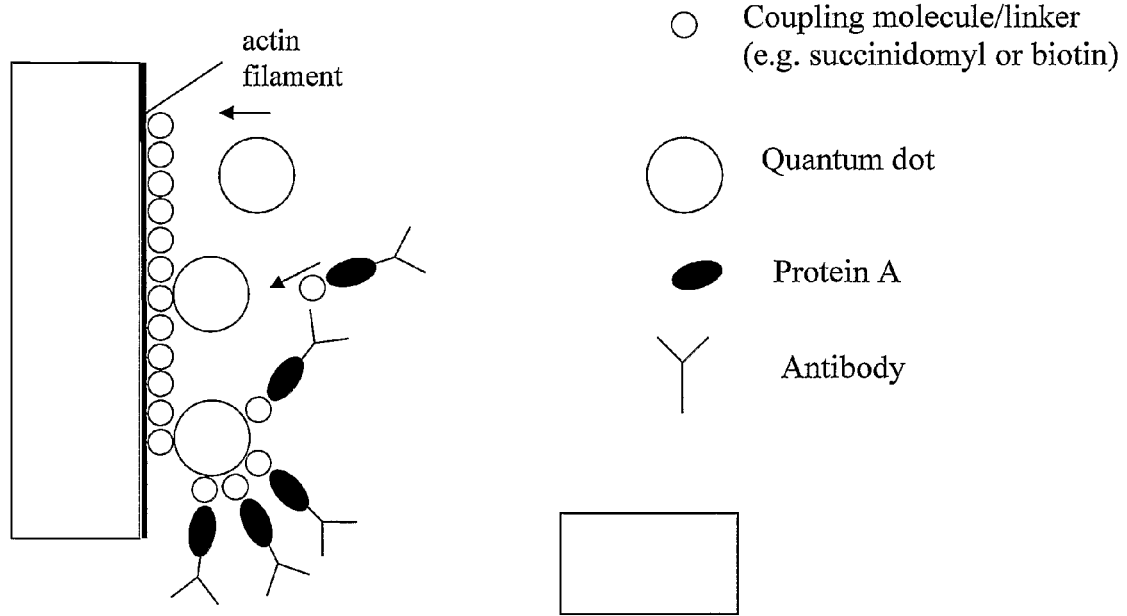
FIG. 3 is a schematic presentation of the labelling of one side of a cytoskeletal filament with quantum dot reporter molecules and recognition elements in the form of antibodies along one side of the filaments as described in Example 6. During the labelling the filament is bound to myosin motors or motor fragments adsorbed to a silanized silicon or glass surface (e.g. silicon beads in a column or the walls of a glass capillary).

If the recognition element is one or more oligonucleotides or nucleic acid fragments to be used for the detection of nucleic acids the binding fragments will be coupled with different parts of the complementary strand directed against the molecule to be identified. Thus, if e.g. a specific mRNA is to be detected some binding fragments will be coupled with oligonucleotides complementary to one part of the mRNA to be detected and other binding fragments will be coupled with oligonucleotides complementary to another part of the mRNA to be detected. When the mRNA to be identified is added it will cross-link the oligonucleotides on two different binding fragments and thus form aggregates of these (see FIG. 2).

Actin filaments are less rigid compared to microtubules in connection with torsion and bending[11]. This increases the possibility that recognition elements on different filaments will cross link the different filaments upon binding to a molecule and for formation of aggregates. When the cross linking has occurred it will be more or less irreversible if no external forces are present. As actin filaments are short (usually <20 μm) they can easily be used in small tubes/wells etc.

Said binding fragment is selected from the group consisting of actin filaments and microtubules or their prokaryotic analogues or mixtures thereof. These fragments may also be chemically modified or synthetically produced.

Each fragment is composed of a large number of identical binding units, the monomers. For instance, each actin filament consists of ~400 identical monomers per 1 μm length of the filament. By varying the conditions for formation of the filaments (e.g. different concentration of monomers, different salt concentrations and the presence of the actin severing protein gelsolin[12]) the length can be varied between less than 100 nm and more than 50 μm. As there is at least one binding site for recognition elements and 1 binding site for reporter molecules on each monomer this opens for the labelling of each actin filament with between 40 and >20 000 recognition elements and reporter molecules.

Said reporter molecules and said recognition elements may be evenly distributed along said binding fragment, e.g. along one side (e.g. Examples 6-7) or, alternatively in a helical arrangement along the helical protofilaments of the filament.

Said binding fragments of said detection conjugate may have the same or different lengths varying between 100 nm and more than 50 μm, such as 1-3, 2-5, 3-6, 3-7, 4-7, 6-10, 10-15, 14-20 or >20 um. Said recognition elements may be directed against a pathogen, toxin or disease marker, such as a specific protein or nucleotide sequence. Examples of relevant pathogens are viruses (e.g. human or avian influenza) and bacteria (e.g. *Eschericia coli* and *Helicobacter pylori*). Examples of toxins are anthrax and botulinum toxin. Finally, examples of relevant disease markers are prostate specific antigen (PSA) for prostate cancer and ABL-BCR fusion mRNA for chronic myeloid leukemia.

Said reporter molecules are selected from the group consisting of coloured substances, fluorochromes, quantum dots, enzymes, and gold, silver and magnetic nanoparticles. The reporter molecule(s) may be bound to said binding fragments through phalloidin-biotin-streptavidin coupling or other similar known coupling methods.

One embodiment concerns the above defined detection conjugate wherein said binding fragment(s) are actin filaments, which easily to low cost can be obtained from muscles (meat), from for example by-products of the meat industry. The actin filaments can also be stored in a freezer for a subset of years without any alteration of their properties. It is also easy to couple biotin along the actin filaments through phalloidin-coupling and even to couple nano-particles to these biotin molecules[8].

The invention aims at analysing/detecting one or more molecule(s) or microorganism(s) in a sample comprising the steps of: Providing a sample, which may be plasma, other body fluids or extracts thereof, cell or tissue extracts, environmental samples from e.g. air, soil or water, extracts from faeces of birds (monitoring of avian influenza) etc., adding said sample to said detection conjugates as defined above leading to aggregation of said detection conjugates signalling the presence of an analyte. Quantitative information about concentration of analyte may be obtained from the amount of aggregates.

Detection of the aggregates can be performed in a number of ways such as by microscopy, light scattering, pelleting by centrifugation etc. Detection using a fluorescence microscope is trivial since even individual fluorescence labelled filaments are readily observed (cf.[13]). However, the formation of large aggregates may also be detected by dark field microscopy due to increased amounts of scattered light or by using differential interference contrast (DIC) microscopy due to increased phase changes of light passing through and by the large filament aggregates. Furthermore, if gold or silver nanoparticles are attached along the filaments surface enhanced Raman scattering and localized surface plasmon resonance effects may be the basis for detection (cf.[2]).

As mentioned above the aggregates may also be detected through precipitation, such as if the aggregates are large enough to precipitate without centrifugation they may be detectable by the naked eye. If they are not large enough to precipitate they can be pelleted by centrifugation at different centrifugal forces depending on the size of the aggregates and then be detected by the naked eye, with or without illumination at specific wavelengths, or by microscopy. By ultracentrifugation it is even possible to pellet individual actin filaments[14].

The determination of the molecules to be detected may be enhanced by different means if there is a need. This may be performed by attaching a higher amount of reporter molecules to said binding fragments which will increase the sensitivity. By increasing the amount of reporter molecules as defined above the detection could be performed by the use of for example absorption spectometry, fluoroscensce spectrometry, surface plasmon resonance and possibly surface enhanced Raman scattering as mentioned above.

It may also be possible to detect several different analytes in one and the same sample by the use of different proportions of both the recognition elements and the reporter molecules. By the use of for example cytoskeletal fragments being labelled with different reporter molecules (e.g. one which emits green light and one which emits red light) in varied proportions the system/method may be developed to detect several different molecules in one and the same sample.

The invention also relates to a kit comprising said detection conjugate as well as a manual how to use said detection conjugate. Said kit may be one or several tubes or test strips in which the entire detection conjugates or the components (binding fragments, recognition elements, reporter molecules) of said detection conjugate or conjugates are placed. Said detection conjugate, or its individual components may be frozen as well as placed in a suitable solution in a free form. Said kit may also involve any suitable micro titre plate as well as an array or chip with inbuilt detection systems. The kit may also comprise other parts such as those mentioned above which are needed for the use of said kit in the analysis of one or more compounds.

The following examples are intended to illustrate, but not to limit, the invention in any manner, shape, or form, either explicitly or implicitly.

EXAMPLES

Example 1

Purification of Actin Filaments

Actin filaments are obtained from G-actin monomers purified from skeletal or heart muscle (e.g. Bovine heart obtained as a by-product in the meat industry). The purification of actin and the formation of filamentous form of the protein are performed according to standard procedures (e.g.[13, 15]).

Example 2

Storage of Actin Filaments

Following the isolation of actin filaments as described above these may be stored at −80° C. for several years without loss of function[13].

Example 3

Stabilization of Actin Filaments by Chemical Modification

The actin filaments can be stabilized by mixing with an equimolar (on monomer basis) concentration of phalloidin as described previously[16].

Example 4

Purification of Microtubules

Tubulin is purified from porcine brain using standard protocols[17].

Example 5

Labelling of Actin Filaments with Reporter Molecules in the Form of Small Fluorophores Small fluorophores suitable as reporter molecules are e.g. tetramethylrhodamine-isothiocyanate-phalloidin or one of the Alexa™-series of dyes coupled to phalloidin[13]. The labelling with these fluorescent dyes is performed using standard protocols[13, 16]. As an alternative to labelling via phalloidin, labelling can be performed by direct covalent attachment of fluorophores to e.g. cysteines or other amino acid residues on each actin (cf.[18]).

Example 6

Simultaneous Labelling of Actin Filaments with Reporter Molecules in the Form of Quantum-Dots and Recognition Elements in the Form of Antibodies Quantum dots (from Molecular Probes Invitrogen or other commercial sources) are attached to a majority of the actin monomers on each given actin filament. Suitable quantum dots characterized by their sharply defined emission wavelengths are used to identify the filaments as labelled with certain specific recognition elements. The labelling aims to produce as many quantum dots per actin filament as possible.

Actin filaments are biotinylated via phalloidin as described in REF, which stabilizes the filaments. Moreover, as shown in reference[13] the biotinylation does not prevent binding to myosin. Neither does it affect the ATP hydrolyzing interaction cycle between actin and myosin where the actomyosin connection is broken by high concentration of ATP.

Actin filaments are captured by myosin coated silicon beads in a suitable column or on the walls of a glass capillary silanized with trimethylchlorosilane[19] and subsequently eluted by high ATP concentration in a solution of high ionic strength[14].

After addition of the biotinylated actin filaments to the myosin coated column streptavidin-coated quantum dots of suitable emission properties are added at nanomolar concentration to the same column. The reaction is allowed to proceed until the quantum dot concentration of the efflux from the column does not differ from the concentration of the added quantum dot solution. Next, biotinylated protein A is added followed by 1 μM biotin to block free biotin-binding sites on streptavidin. Finally, the actin filaments are eluted from the column by addition of ATP in a high ionic strength solution thus breaking the actomyosin interaction. Following this elution the actin filaments are pelleted by ultracentrifugation at 200 000 g for 40 min and subsequently dissolved to a considerably higher concentration as desired.

In the next step, the actin filaments are labelled with suitable antibodies that bind, via their Fc-fragments to protein A. This procedure follows that described in reference[20] with mixing of suitable antibodies at 0.01-1 g/l with the filaments (0.01-1 μM) in phosphate buffered saline for 2 h to obtain different degree of coverage of the filaments with antibodies.

Labelling of filaments with gold or silver nanoparticles or with magnetic nanoparticles can be achieved by a similar method as that described here for the labelling with quantum dots.

Example 7

Simultaneous Labelling of Actin Filaments with Reporter Molecules in the Form of Quantum-dots and Recognition Elements in the Form of Oligonucleotides Biotinylated actin filaments are labeled with streptavidin-coated quantum dots in a myosin coated column as in Example 6. Next, biotinylated sequence specific oligonucleotides (e.g. 10-20 nucleotides long biotin labelled by e.g. the 3'EndTag DNA Labelling System or the 5'EndTag Nucleic Acid Labelling System, Vector laboratories) are added followed by 1 μM biotin to block free biotin-binding sites on streptavidin. The oligonucleotide sequence is designed to be complementary to one part of a specific mRNA to be detected. In a separate column actin filaments are similarly labelled with another oligonucleotide with a sequence complementary to another part of a specific mRNA to be detected. Finally, the actin filaments are eluted from the columns by addition of ATP in a high ionic strength solution as described in Example 6. Following this elution the actin filaments are pelleted by ultracentrifugation at 200 000 g for 40 min and subsequently dissolved at a desired concentration.

Example 8

Labelling of Microtubules with Reporter Molecules in the Form of Quantum-Dots This labelling has the same goals and is performed as described for the actin filaments above but instead of the myosin column a kinesin column is used.

Example 9

Labelling of Actin Filaments or Microtubules that Contain Small-Molecular Fluorescent Reporter Molecules with Recognition Elements in the Form of Antibodies Recognition elements in the form of antibodies are attached to actin filaments or microtubules subsequent to labelling with small-molecular fluorescent reporter molecules according to standard procedures (Ref, Ref). First, carboxyl groups on the surface of the filaments are activated by treatment with 20 mM N-hydroxysuccinimide (NHS) and 10 mM N-(3-dimethylaminopropyl)-N'-ethylcarbodiimide hydrochloride (EDC) dissolved in a buffered solution (pH 7.4) containing 2 mM $MgCl_2$ and 50 mM KCl. Next the filaments (1 μM) are immersed in a solution with Protein A (10 mg/l) in 10 mM PBS, pH 7.4 for 2 h (cf.[20]). ProteinA-coated filaments are next incubated in a solution with suitable IgG antibodies at concentrations from 0.1-1 g/l in PBS for 2 h. The antibody-labelled filaments are collected by ultracentrifugation at 200000 g for 40 min. The supernatant is discarded whereas the pellet is re-dissolved in a suitable buffered, solution e.g. containing 0.1 mM ATP, 2 mM $MgCl_2$ and 150 mM KCl for actin filaments.

Example 10

Detection of the ABL-BCR Transcript as a Disease Marker for Chronic Myeloid Leukemia In chronic myeloid leukemia a chimeric ABL-BCR fusion mRNA is expressed as a result of a chromosomal translocation leading to the fusion of parts of the two genes ABL and BCR[21]. Actin filaments are labelled as in Example 7 such that some filaments carry an oligonucleotide complementary to part of the ABL mRNA whereas other filaments carry an oligonucleotide complementary to part of the BCR mRNA. RNA is extracted from cells or tissue to be studied e.g. as described in reference[22]. The isolated RNA is added to a mixture of actin filaments carrying the two different oligonucleotides. If ABL-BCR fusion mRNA is present actin filaments will be cross-linked by the fusion mRNA and aggregate. If only normal ABL and BCR mRNAs are present no aggregation of filaments will occur.

Example 11

A Method to Detect any One of Five Different Influenza Virus Types

Actin filaments are labelled with reporter molecules and recognition elements using any of the techniques described in the examples above. The actin filaments are labelled in such a way that each individual filament contains only one of five different antibodies which are directed against five different virus types. The five different types of actin filaments (labelled with the five different antibodies) are labelled with different proportions of two different reporter molecules (e.g. two different Alexa compounds emitting red and green fluorescence respectively). Thus, e.g. actin filaments labelled with antibody #1 emit only green fluorescence, actin filaments labelled with antibody #2 emit only red fluorescence, actin filaments labelled with antibody #3 emit red and green fluorescence in a ratio 50/50, actin filaments labelled with antibody #4 emit red and green fluorescence in a ratio 25/75 and actin filaments labelled with antibody #5 emit red and green fluorescence in a ratio 75/25. The five different types of actin filaments are mixed in equal proportions. A sample containing an influenza virus is added. The actin filaments containing antibodies directed against this virus type will aggregate. By measuring the ratio of green and red fluorescence in the aggregate the virus type will be determined.

Example 12

A Method to Detect any Combination of Seven Different Pathogens

Actin filaments are labelled with quantum dots and antibodies as described in Example 6. The actin filaments are labelled in such a way that each individual filament contains only one of seven different antibodies directed against seven different pathogens. The seven different types of actin filaments (labelled with the seven different antibodies) are labelled with different quantum dots that emit fluorescence of different wavelengths. Thus, each actin filament has a unique combination of recognition element and reporter molecule and will only recognize and report (by aggregation) one specific pathogen. The seven different types of actin filaments are mixed in equal proportions. A mixture of pathogens is added and actin filaments will aggregate according to which pathogens are present in the sample. The types of pathogens present is determined by the fluorescence at different wavelengths of the aggregated filaments or alternatively by comparing the fluorescence of unaggregated filaments with the fluorescence of filaments before addition of pathogens.

References

1. Pejcic B, et al. (2006) *Analyst* 131:1079
2. Niemeyer C M & C A Mirkin (2004) Nanobiotechnology: concepts, applications and perspectives *Wiley-VCH*
3. D'Orazio P (2003) *Clin Chim Acta* 334:41
4. Zheng G, et al. (2005) *Nat Biotechnol* 23:1294
5. Besteman K, et al. (2003) *Nano Letters* 3:727
6. Ghatnekar-Nilsson S, et al. (2005) *Nanotechnology* 16:98
7. Nam J M, et al. (2003) *Science* 301:1884
8. Månsson A, et al. (2004) *Biochem Biophys Res Commun* 314:529
9. Bachand G D, et al. (2006) *Small* 2:381
10. Ramachandran S, et al. (2006) *Small* 2:330
11. Gittes F, et al. (1993) *Journal of Cell Biology* 120:923
12. Kinosian H J, et al. (1998) *Biophys J* 75:3101
13. Balaz M & A Mansson (2005) *Anal Biochem* 338:224
14. Homsher E, et al. (1992) *Am J Physiol* 262:C714
15. Pardee J D & J A Spudich (1982) *Methods Cell Biol* 24:271
16. Kron S J, et al. (1991) *Methods Enzymol* 196:399
17. Walker R A, et al. (1988) *Journal of Cell Biology* 107:1437
18. Sase I, et al. (1995) *Biophysical Journal* 69:323
19. Sundberg M, et al. (2003) *Anal Biochem* 323:127
20. Briand E, et al. (2006) *Colloids Surf B Biointerfaces* 53:215
21. Smith D L, et al. (2003) *Expert Rev Mol Med* 5:1
22. Cathala G, et al. (1983) *DNA* 2:329

The invention claimed is:

1. A detection system in a solution or in a gel comprising cytoskeletal filaments each with recognition elements coupled to the cytoskeletal filaments covalently or via non-covalent specific affinity coupling, the recognition elements selected from the group consisting of monoclonal antibodies, polyclonal antibodies, Fab-fragments, chimeric proteins, lectins, receptor proteins, nucleic acids, oligonucleotides, aptamers, peptides, or chemical compounds, which in the presence of at least one analyte molecule, cross-link and aggregate via their bound recognition element(s).

2. The detection system according to claim 1, wherein said cytoskeletal filaments are selected from the group consisting of actin filaments and microtubules.

3. The detection system according to claim 1, wherein the said cytoskeletal filaments are labelled with between from about 10 and to about 20 000 or more copies of said recognition element.

4. The detection system according to claim 1, wherein said recognition elements are evenly distributed along said cytoskeletal filaments.

5. The detection system according to claim 1, wherein said system comprises at least one reporter molecule.

6. The detection system according to claim 5, wherein said cytoskeletal filaments are labelled with between 1 and about 20,000 or more copies of said reporter molecule.

7. The detection system according to claim 1, wherein said recognition elements and said reporter molecules are evenly distributed along said cytoskeletal filaments, such as along one side or, alternatively in a helical arrangement along helical proto filaments of said cytoskeletal filaments.

8. The detection system according to claim 1, wherein said cytoskeletal filaments have a length of from about 100 nm to about 50 μm or more.

9. The detection system according to claim 1, wherein different recognition elements are linked/coupled to said cytoskeletal filaments.

10. The detection system according to claim 1, wherein said recognition elements are recognition elements for a pathogen, toxin or disease marker.

11. The detection system according to claim 1, wherein said reporter molecule is selected from the group consisting of coloured substances, fluorochromes, quantum dots, enzymes, gold, silver or magnetic nanoparticles.

12. A method of detecting a molecule or microorganism/pathogen comprising the steps of:
   a. providing a sample,
   b. Adding said sample to said detection system according to claim 1 and
   c. Detecting said molecule or microorganism/pathogen by detecting crosslinking of at least two cytoskeletal filaments with recognition elements.

13. The method according to claim 12, wherein said detection is monitored/registered by a microscope, light scattering, pelleting by centrifugation, spectrophotometry, fluorescence detection, surface enhanced Raman scattering, or surface plasmon resonance.

14. The method according to claim 12 wherein said sample is selected from the group consisting of water, soil, air and biological samples such as plasma, other body fluids or extracts thereof, cell or tissue extracts, extracts from faeces of birds and other species.

\* \* \* \* \*